US008242077B2

(12) United States Patent
Lakey et al.

(10) Patent No.: US 8,242,077 B2
(45) Date of Patent: Aug. 14, 2012

(54) BIOSENSOR

(75) Inventors: Jeremy Hugh Lakey, Northumberland (GB); Horst Vogel, Preverenges (CH)

(73) Assignee: Newcastle University Ventures Limited, Newcastle Upon Tyne (GB)

( * ) Notice: Subject to any disclaimer, the term of this patent is extended or adjusted under 35 U.S.C. 154(b) by 759 days.

(21) Appl. No.: 12/232,393

(22) Filed: Sep. 16, 2008

(65) Prior Publication Data
US 2011/0111985 A1   May 12, 2011

Related U.S. Application Data

(63) Continuation of application No. 10/250,682, filed as application No. PCT/GB02/00222 on Jan. 18, 2002, now abandoned.

(30) Foreign Application Priority Data

Jan. 18, 2001 (GB) .................................. 0101279.8
Apr. 10, 2001 (GB) .................................. 0108947.3

(51) Int. Cl.
*A61K 38/00* (2006.01)
(52) U.S. Cl. ..................................................... 514/17.4
(58) Field of Classification Search ........................ None
See application file for complete search history.

(56) References Cited

U.S. PATENT DOCUMENTS

| 5,234,566 A | 8/1993 | Osman et al. ................. 204/403 |
| 5,516,890 A | 5/1996 | Tomich et al. ................ 530/326 |
| 5,736,342 A | 4/1998 | Wan Wie et al. ............... 435/7.2 |

FOREIGN PATENT DOCUMENTS

| JP | 2000146976 | 5/2000 |
| WO | WO97/25616 | 7/1997 |
| WO | WO99/49026 | 9/1999 |

OTHER PUBLICATIONS

H. Sorribas, "Neurite outgrowth on microstructured surfaces functionalized by a neural adhesion protein," Journal of Materials Science: Materials in Medicine 10, pp. 787-791 (1999).
Stora, T, et al, Ion-Channel Gating in Transmembrane Receptor Proteins: Functional Activity in Tethered Lipid Membranes, Angew. Chem. Int. Ed. (1999) vol. 38, pp. 389-392 (Applicant's IDS).
Kanno S, "Assembling of engineered IgG-binding protein on gold surface for highly oriented antibody immobilization," J Biotechnol. Jan. 21, 2000;76(2-3):207-14.
Koebnik R, "Structure and function of bacterial outer membrane proteins: barrels in a nutshell," Mol Microbiol. Jul. 2000;37(2):239-53.
Lang et al, A New Class of Thiolipids for the Attachment of Lipid Bilayers on Gold Surfaces, Langmuir (1994), 10, 197-210 (Applicant's IDS).
Feng Y, Davis NG., "Feedback phosphorylation of the yeast a-factor receptor requires activation of the downstream signaling pathway from G protein through mitogen-activated protein kinase," Mol Cell Biol. Jan. 2000;20(2):563-74.

Heyse et al, Biochimica et Biophysica Acta 85507, pp. 319-338, 1998, Emerging techniques for investigating molecular . . . .
Hong et al, Biochemical Society Transactions, vol. 29, Part 4, 2001, pp. 578-582, Assembly of pore proteins on gold electrodes.
Bieri et al, Nature Biotechnology, vol. 17, Nov. 1999 pp. 1105-1108, Micropatterned immobilization of a G protein-coupled . . . .
Bainbridge et al, J. Mol. Biol. 275, pp. 171-176, 1998, Voltage gating of *Escherichia coli* Porin: A Cystine-scanning . . . .
Heyse et al, Biochemistry 37, pp. 507-522, 1998 Incorporation of Rhodopsin in Laterally Structured Supported Membranes: . . . .
Cornell et al, Letters to Nature, vol. 387, pp. 580-583, Jun. 5, 1997 A biosensor that uses ion-channel switches.
Stora et al, Angew. Chem. Int. Ed., vol. 38, No. 3, pp. 389-392 1999, Ion-Channel Gating in Transmembrane Receptor Proteins . . . .
Evans et al, J. Mol. Biol. 255, pp. 559-563, 1996, Direct Measurement of the Association of a Protein with a Family of . . . .
Nabedryk et al, Biophys. J., vol. 53, pp. 671-676, May 1988, The Orientation of β-Sheets in Porin. A Polarized Fourier . . . .
Evans, et al, Biochemistry 35, pp. 15143-15148, 1996, The Central Domain of Colicin N Possesses the Receptor . . . .
Lang et al, Langmuir 10, pp. 197-210, 1994, A New Class of Thiolipids for the Attachment of Lipid Bilayers on Gold Surfaces.
Boncheva et al, Biophysical Journal, vol. 73, pp. 1056-1072, Aug. 1997, Formation of Stable Polypeptide Monolayers at . . . .
Arora et al, Nature Structural Biology, vol. 8, No. 4, Apr. 2001 pp. 334-338, Structure of outer membrane protein A . . . .
Kleinschmidt et al, Protein Science, pp. 2065-2071, 1999, Outer membrane protein A of *E. coli* folds into detergent micelles, . . . .
Pautsch et al, J. Mol. Biol. 298, pp. 273-282, 2000, High-resolution Structure of the OmpA Membrane Domain.
Duschl, C. et al., "Sulphur-bearing Lipids for the Covalent Attachment of Supported Lipid Bilayers to Gold Surfaces: a Detailed Characterisation and Analysis" Materials Science and Engineering C (1996) pp. 7-18, vol. 4.
Hong, H.G. et al., "Cysteine-Specific Surface Tethering of Genetically Engineered Cytochromes for Fabrication of Metalloprotein NanostructureS" Langmuir (1994) pp. 153-158, vol. 10, No. 1.
Vigmond, S.J. et al., "Site-Specific Immobilization of Molecular Engineered Dihydrofolate Reductase to Gold Surfaces" Langmuir (1994) pp. 2860-2862, vol. 10, No. 9.
Damrongchai, N. et al., "Self-assembling of Glutathione S-transferase/calmodulin Fusion Protein on Chemically Modified Gold Surface" Journal of Biotechnology (1997) pp. 125-133, vol. 55.

*Primary Examiner* — Cecilia J Tsang
*Assistant Examiner* — Thomas Heard
(74) *Attorney, Agent, or Firm* — Scully, Scott, Murphy & Presser, P.C.

(57) ABSTRACT

The invention provides a product comprising: a membrane-spanning protein; a lipid membrane formed from amphiphilic molecules and membrane-spanning protein molecules; and a substrate, wherein the membrane protein is directly coupled to the substrate. The invention also provides a method for producing such a product which i) comprises treating a substrate with a hydrophilic coating agent; ii) providing at least one membrane-spanning protein; iii) bringing the protein into contact with the treated substrate under conditions for the coupling of the protein directly to the treated substrate; and iv) adding amphiphilic molecules to the protein-coupled substrate to form a lipid membrane. The product is useful for biosensors, protein arrays and the like.

18 Claims, 3 Drawing Sheets

Figure 2:
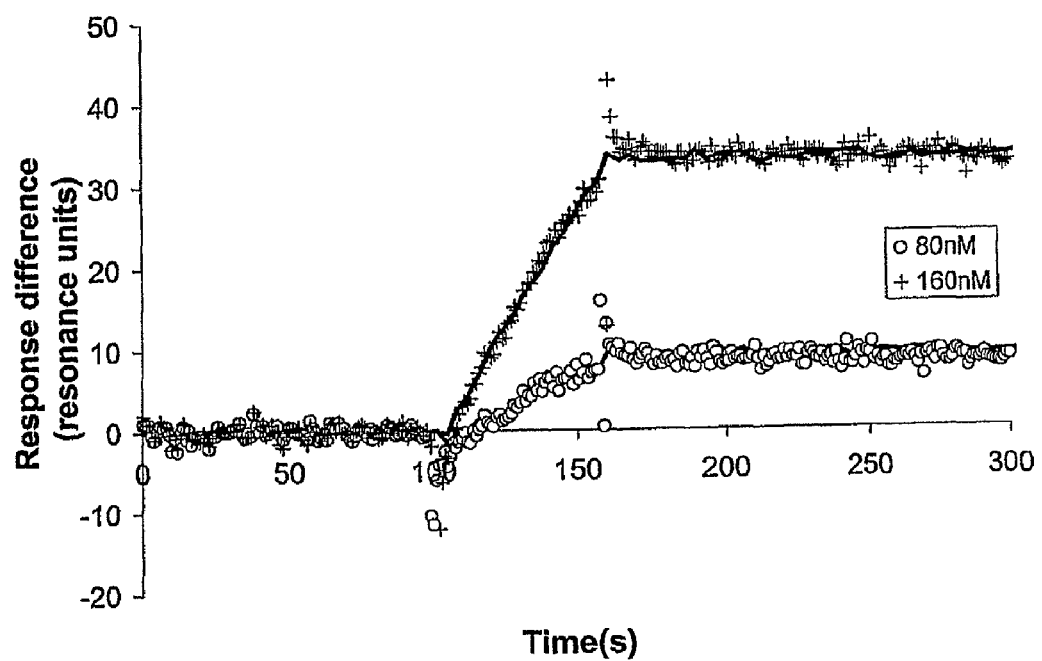

| | | | | | | | | | | | | | | |
|---|---|---|---|---|---|---|---|---|---|---|---|---|---|---|
| atg | atg | aag | cgc | aat | att | ctg | gca | gtg | atc | gtc | cct | gct | ctg | tta | gta | 48 |
| Met | Met | Lys | Arg | Asn | Ile | Leu | Ala | Val | Ile | Val | Pro | Ala | Leu | Leu | Val |
| 1 | | | | 5 | | | | | 10 | | | | | 15 | |
| gca | ggt | act | gca | aac | gct | gca | gaa | atc | tat | aac | aaa | gat | ggc | aac | aaa | 96 |
| Ala | Gly | Thr | Ala | Asn | Ala | Ala | Glu | Ile | Tyr | Asn | Lys | Asp | Gly | Asn | Lys |
| | | | 20 | | | | | 25 | | | | | 30 | | |
| gta | gat | ctg | tac | ggt | aaa | gct | gtt | ggt | ctg | cat | tat | ttt | tcc | aag | ggt | 144 |
| Val | Asp | Leu | Tyr | Gly | Lys | Ala | Val | Gly | Leu | His | Tyr | Phe | Ser | Lys | Gly |
| | | 35 | | | | | 40 | | | | | 45 | | | |
| aac | ggt | gaa | aac | agt | tac | ggt | ggc | aat | ggc | gac | atg | acc | tat | gcc | cgt | 192 |
| Asn | Gly | Glu | Asn | Ser | Tyr | Gly | Gly | Asn | Gly | Asp | Met | Thr | Tyr | Ala | Arg |
| | 50 | | | | | 55 | | | | | 60 | | | | |
| ctt | ggt | ttt | aaa | ggg | gaa | act | caa | atc | aat | tcc | gat | ctg | acc | ggt | tat | 240 |
| Leu | Gly | Phe | Lys | Gly | Glu | Thr | Gln | Ile | Asn | Ser | Asp | Leu | Thr | Gly | Tyr |
| 65 | | | | | 70 | | | | | 75 | | | | | 80 |
| ggt | cag | tgg | gaa | tat | aac | ttc | cag | ggt | aac | aac | tct | gaa | ggc | gct | gac | 288 |
| Gly | Gln | Trp | Glu | Tyr | Asn | Phe | Gln | Gly | Asn | Asn | Ser | Glu | Gly | Ala | Asp |
| | | | | 85 | | | | | 90 | | | | | 95 | |
| gct | caa | act | ggt | aac | aaa | acg | cgt | ctg | gca | ttc | gcg | ggt | ctt | aaa | tac | 336 |
| Ala | Gln | Thr | Gly | Asn | Lys | Thr | Arg | Leu | Ala | Phe | Ala | Gly | Leu | Lys | Tyr |
| | | | 100 | | | | | 105 | | | | | 110 | | |
| gct | gac | gtt | ggt | tct | ttc | gat | tac | ggc | cgt | aac | tac | ggt | gtg | gtt | tat | 384 |
| Ala | Asp | Val | Gly | Ser | Phe | Asp | Tyr | Gly | Arg | Asn | Tyr | Gly | Val | Val | Tyr |
| | | 115 | | | | | 120 | | | | | 125 | | | |
| gat | gca | ctg | ggt | tac | acc | gat | atg | ctg | cca | gaa | ttt | ggt | ggt | gat | act | 432 |
| Asp | Ala | Leu | Gly | Tyr | Thr | Asp | Met | Leu | Pro | Glu | Phe | Gly | Gly | Asp | Thr |
| | 130 | | | | | 135 | | | | | 140 | | | | |
| gca | tac | agc | gat | gac | ttc | ttc | gtt | ggt | cgt | gtt | ggc | ggc | gtt | gct | acc | 480 |
| Ala | Tyr | Ser | Asp | Asp | Phe | Phe | Val | Gly | Arg | Val | Gly | Gly | Val | Ala | Thr |
| 145 | | | | | 150 | | | | | 155 | | | | | 160 |
| tat | cgt | aac | tcc | aac | ttc | ttt | ggt | ctg | gtt | gat | ggc | ctg | aac | ttc | gct | 528 |
| Tyr | Arg | Asn | Ser | Asn | Phe | Phe | Gly | Leu | Val | Asp | Gly | Leu | Asn | Phe | Ala |
| | | | | 165 | | | | | 170 | | | | | 175 | |
| gtt | cag | tac | ctg | ggt | aaa | aac | gag | cgt | gac | act | gca | cgc | cgt | tct | aac | 576 |
| Val | Gln | Tyr | Leu | Gly | Lys | Asn | Glu | Arg | Asp | Thr | Ala | Arg | Arg | Ser | Asn |
| | | | 180 | | | | | 185 | | | | | 190 | | |
| ggc | gac | ggt | gtt | ggc | ggt | tct | atc | agc | tac | gaa | tac | gaa | ggc | ttt | ggt | 624 |
| Gly | Asp | Gly | Val | Gly | Gly | Ser | Ile | Ser | Tyr | Glu | Tyr | Glu | Gly | Phe | Gly |
| | | 195 | | | | | 200 | | | | | 205 | | | |

Figure 1 (continued on next page)

```
atc gtt ggt gct tat ggt gca gct gac cgt acc aac ctg caa gaa gct    672
Ile Val Gly Ala Tyr Gly Ala Ala Asp Arg Thr Asn Leu Gln Glu Ala
    210                 215                 220
caa cct ctt ggc aac ggt aaa aaa gct gaa cag tgg gct act ggt ctg    720
Gln Pro Leu Gly Asn Gly Lys Lys Ala Glu Gln Trp Ala Thr Gly Leu
225                 230                 235                 240
aag tac gac gcg aac aac atc tac ctg gca gcg aac tac ggt gaa acc    768
Lys Tyr Asp Ala Asn Asn Ile Tyr Leu Ala Ala Asn Tyr Gly Glu Thr
                    245                 250                 255
cgt aac gct acg ccg atc act aat aaa ttt aca aac acc agc ggc ttc    816
Arg Asn Ala Thr Pro Ile Thr Asn Lys Phe Thr Asn Thr Ser Gly Phe
                260                 265                 270
gcc aac aaa acg caa gac gtt ctg tta gtt gcg caa tac cag ttc gat    864
Ala Asn Lys Thr Gln Asp Val Leu Leu Val Ala Gln Tyr Gln Phe Asp
            275                 280                 285
ttc ggt ctg cgt ccg tcc atc gct tac acc aaa tct aaa gcg aaa gac    912
Phe Gly Leu Arg Pro Ser Ile Ala Tyr Thr Lys Ser Lys Ala Lys Asp
        290                 295                 300
gta gaa ggt atc ggt gat gtt gat ctg gtg aac tac ttt gaa gtg ggc    960
Val Glu Gly Ile Gly Asp Val Asp Leu Val Asn Tyr Phe Glu Val Gly
305                 310                 315                 320
gca acc tac tac ttc aac aaa aac atg tcc acc tat gtt gac tac atc   1008
Ala Thr Tyr Tyr Phe Asn Lys Asn Met Ser Thr Tyr Val Asp Tyr Ile
                325                 330                 335
atc aac cag atc gat tct gac aac aaa ctg ggc gta ggt tca gac gac   1056
Ile Asn Gln Ile Asp Ser Asp Asn Lys Leu Gly Val Gly Ser Asp Asp
            340                 345                 350
acc gtt gct gtg ggt atc gtt tac cag ttc taa                       1089
Thr Val Ala Val Gly Ile Val Tyr Gln Phe
        355                 360
```

Figure 1 (continued)

SEQUENCE LISTING

<160> NUMBER OF SEQ ID NOS: 8

<210> SEQ ID NO 1
<211> LENGTH: 1089
<212> TYPE: DNA
<213> ORGANISM: Escherichia coli
<220> FEATURE:
<221> NAME/KEY: CDS
<222> LOCATION: (1)..(1089)

<400> SEQUENCE: 1

```
atg atg aag cgc aat att ctg gca gtg atc gtc cct gct ctg tta gta      48
Met Met Lys Arg Asn Ile Leu Ala Val Ile Val Pro Ala Leu Leu Val
1               5                   10                  15 gca ggt act gca aac gct gca gaa atc tat aac aaa gat ggc aac aaa      96
Ala Gly Thr Ala Asn Ala Ala Glu Ile Tyr Asn Lys Asp Gly Asn Lys
                20                  25                  30 gta gat ctg tac ggt aaa gct gtt ggt ctg cat tat ttt tcc aag ggt     144
Val Asp Leu Tyr Gly Lys Ala Val Gly Leu His Tyr Phe Ser Lys Gly
            35                  40                  45 aac ggt gaa aac agt tac ggt ggc aat ggc gac atg acc tat gcc cgt     192
Asn Gly Glu Asn Ser Tyr Gly Gly Asn Gly Asp Met Thr Tyr Ala Arg
        50                  55                  60 ctt ggt ttt aaa ggg gaa act caa atc aat tcc gat ctg acc ggt tat     240
Leu Gly Phe Lys Gly Glu Thr Gln Ile Asn Ser Asp Leu Thr Gly Tyr
65                  70                  75                  80 ggt cag tgg gaa tat aac ttc cag ggt aac aac tct gaa ggc gct gac     288
Gly Gln Trp Glu Tyr Asn Phe Gln Gly Asn Asn Ser Glu Gly Ala Asp
                85                  90                  95 gct caa act ggt aac aaa acg cgt ctg gca ttc gcg ggt ctt aaa tac     336
```

| | | |
|---|---|---|
| Ala Gln Thr Gly Asn Lys Thr Arg Leu Ala Phe Ala Gly Leu Lys Tyr<br>100                          105                    110 | | |

```
gct gac gtt ggt tct ttc gat tac ggc cgt aac tac ggt gtg gtt tat       384
Ala Asp Val Gly Ser Phe Asp Tyr Gly Arg Asn Tyr Gly Val Val Tyr
        115                 120                 125 gat gca ctg ggt tac acc gat atg ctg cca gaa ttt ggt ggt gat act       432
Asp Ala Leu Gly Tyr Thr Asp Met Leu Pro Glu Phe Gly Gly Asp Thr
130                 135                 140 gca tac agc gat gac ttc ttc gtt ggt cgt gtt ggc ggc gtt gct acc       480
Ala Tyr Ser Asp Asp Phe Phe Val Gly Arg Val Gly Gly Val Ala Thr
145                 150                 155                 160 tat cgt aac tcc aac ttc ttt ggt ctg gtt gat ggc ctg aac ttc gct       528
Tyr Arg Asn Ser Asn Phe Phe Gly Leu Val Asp Gly Leu Asn Phe Ala
                165                 170                 175 gtt cag tac ctg ggt aaa aac gag cgt gac act gca cgc cgt tct aac       576
Val Gln Tyr Leu Gly Lys Asn Glu Arg Asp Thr Ala Arg Arg Ser Asn
        180                 185                 190 ggc gac ggt gtt ggc ggt tct atc agc tac gaa tac gaa ggc ttt ggt       624
Gly Asp Gly Val Gly Gly Ser Ile Ser Tyr Glu Tyr Glu Gly Phe Gly
                195                 200                 205 atc gtt ggt gct tat ggt gca gct gac cgt acc aac ctg caa gaa gct       672
Ile Val Gly Ala Tyr Gly Ala Ala Asp Arg Thr Asn Leu Gln Glu Ala
210                 215                 220 caa cct ctt ggc aac ggt aaa aaa gct gaa cag tgg gct act ggt ctg       720
Gln Pro Leu Gly Asn Gly Lys Lys Ala Glu Gln Trp Ala Thr Gly Leu
225                 230                 235                 240 aag tac gac gcg aac aac atc tac ctg gca gcg aac tac ggt gaa acc       768
Lys Tyr Asp Ala Asn Asn Ile Tyr Leu Ala Ala Asn Tyr Gly Glu Thr
                245                 250                 255 cgt aac gct acg ccg atc act aat aaa ttt aca aac acc agc ggc ttc       816
Arg Asn Ala Thr Pro Ile Thr Asn Lys Phe Thr Asn Thr Ser Gly Phe
        260                 265                 270 gcc aac aaa acg caa gac gtt ctg tta gtt gcg caa tac cag ttc gat       864
Ala Asn Lys Thr Gln Asp Val Leu Leu Val Ala Gln Tyr Gln Phe Asp
275                 280                 285 ttc ggt ctg cgt ccg tcc atc gct tac acc aaa tct aaa gcg aaa gac       912
Phe Gly Leu Arg Pro Ser Ile Ala Tyr Thr Lys Ser Lys Ala Lys Asp
                290                 295                 300 gta gaa ggt atc ggt gat gtt gat ctg gtg aac tac ttt gaa gtg ggc       960
Val Glu Gly Ile Gly Asp Val Asp Leu Val Asn Tyr Phe Glu Val Gly
305                 310                 315                 320 gca acc tac tac ttc aac aaa aac atg tcc acc tat gtt gac tac atc      1008
Ala Thr Tyr Tyr Phe Asn Lys Asn Met Ser Thr Tyr Val Asp Tyr Ile
                325                 330                 335 atc aac cag atc gat tct gac aac aaa ctg ggc gta ggt tca gac gac      1056
Ile Asn Gln Ile Asp Ser Asp Asn Lys Leu Gly Val Gly Ser Asp Asp
        340                 345                 350 acc gtt gct gtg ggt atc gtt tac cag ttc taa                          1089
Thr Val Ala Val Gly Ile Val Tyr Gln Phe
                355                 360

<210> SEQ ID NO 2
<211> LENGTH: 362
<212> TYPE: PRT
<213> ORGANISM: Escherichia coli

<400> SEQUENCE: 2

Met Met Lys Arg Asn Ile Leu Ala Val Ile Val Pro Ala Leu Leu Val
1               5                   10                  15

Ala Gly Thr Ala Asn Ala Ala Glu Ile Tyr Asn Lys Asp Gly Asn Lys
            20                  25                  30
```

Val Asp Leu Tyr Gly Lys Ala Val Gly Leu His Tyr Phe Ser Lys Gly
         35                  40                  45

Asn Gly Glu Asn Ser Tyr Gly Asn Gly Asp Met Thr Tyr Ala Arg
 50                  55                  60

Leu Gly Phe Lys Gly Glu Thr Gln Ile Asn Ser Asp Leu Thr Gly Tyr
 65                  70                  75                  80

Gly Gln Trp Glu Tyr Asn Phe Gln Gly Asn Asn Ser Glu Gly Ala Asp
                 85                  90                  95

Ala Gln Thr Gly Asn Lys Thr Arg Leu Ala Phe Ala Gly Leu Lys Tyr
            100                 105                 110

Ala Asp Val Gly Ser Phe Asp Tyr Gly Arg Asn Tyr Gly Val Val Tyr
            115                 120                 125

Asp Ala Leu Gly Tyr Thr Asp Met Leu Pro Glu Phe Gly Gly Asp Thr
130                 135                 140

Ala Tyr Ser Asp Asp Phe Phe Val Gly Arg Val Gly Gly Val Ala Thr
145                 150                 155                 160

Tyr Arg Asn Ser Asn Phe Phe Gly Leu Val Asp Gly Leu Asn Phe Ala
                165                 170                 175

Val Gln Tyr Leu Gly Lys Asn Glu Arg Asp Thr Ala Arg Arg Ser Asn
            180                 185                 190

Gly Asp Gly Val Gly Gly Ser Ile Ser Tyr Glu Tyr Glu Gly Phe Gly
            195                 200                 205

Ile Val Gly Ala Tyr Gly Ala Ala Asp Arg Thr Asn Leu Gln Glu Ala
            210                 215                 220

Gln Pro Leu Gly Asn Gly Lys Lys Ala Glu Gln Trp Ala Thr Gly Leu
225                 230                 235                 240

Lys Tyr Asp Ala Asn Asn Ile Tyr Leu Ala Ala Asn Tyr Gly Glu Thr
                245                 250                 255

Arg Asn Ala Thr Pro Ile Thr Asn Lys Phe Thr Asn Thr Ser Gly Phe
            260                 265                 270

Ala Asn Lys Thr Gln Asp Val Leu Leu Val Ala Gln Tyr Gln Phe Asp
            275                 280                 285

Phe Gly Leu Arg Pro Ser Ile Ala Tyr Thr Lys Ser Lys Ala Lys Asp
            290                 295                 300

Val Glu Gly Ile Gly Asp Val Asp Leu Val Asn Tyr Phe Glu Val Gly
305                 310                 315                 320

Ala Thr Tyr Tyr Phe Asn Lys Asn Met Ser Thr Tyr Val Asp Tyr Ile
                325                 330                 335

Ile Asn Gln Ile Asp Ser Asp Asn Lys Leu Gly Val Gly Ser Asp Asp
            340                 345                 350

Thr Val Ala Val Gly Ile Val Tyr Gln Phe
            355                 360

<210> SEQ ID NO 3
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 3
ggttctatca gctactgtta cgaaggcttt ggtatcg         37

<210> SEQ ID NO 4
<211> LENGTH: 37
<212> TYPE: DNA

```
<213> ORGANISM: Artificial Sequence
<220> FEATURE:
<223> OTHER INFORMATION: Synthetic oligonucleotide

<400> SEQUENCE: 4
ccaagatagt agatgacaat gcttccgaaa ccatagc                                37

<210> SEQ ID NO 5
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 5
ttttctcgag ctgtgctccg aaagataaca cc                                     32

<210> SEQ ID NO 6
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 6
ttttgcgcaa agtgccacgg cctcgacctc g                                      31

<210> SEQ ID NO 7
<211> LENGTH: 9
<212> TYPE: PRT
<213> ORGANISM: Artificial Sequence
<220> FEATURE:
<223> OTHER INFORMATION: N-terminal tag sequence encoded by pET8c
      vector

<400> SEQUENCE: 7

Met His His His His His His Ser Ser
1               5

<210> SEQ ID NO 8
<211> LENGTH: 10
<212> TYPE: PRT
<213> ORGANISM: Artificial Sequence
<220> FEATURE:
<223> OTHER INFORMATION: Synthesized

<400> SEQUENCE: 8

Met His His His His His His Ser Ser Cys
1               5                   10
```

BIOSENSOR

This application is a Continuation Application of U.S. patent application Ser. No. 10/250,682 filed Oct. 17, 2003, now abandoned which is a National Stage application of PCT/GB02/00222 filed Jan. 18, 2002.

TECHNICAL FIELD

The invention relates to a product, typically referred to as a biosensor, comprising a membrane-spanning protein linked to a substrate, including methods to manufacture the product and uses thereof.

BACKGROUND

Amphiphilic molecules, for example lipids, are known to aggregate in solution to form membrane structures which may be monolayers, micelles or liposomes. These structures have been shown to have semi-permeable properties which, in some examples, show selective passage of molecules (eg ions, ligands, antagonists, agonists). The selective permeability relates to the chemistry of the lipids used in the construction of the membrane structures. It is also known that these synthetic membranes may incorporate larger molecules such as polypeptides or proteins which function to, for example, facilitate the transport of molecules (for example, ion-channels which facilitate the transport of ions across membranes are referred to as ionophores), act as receptors for ligands, form pores through which polypeptides may be translocated (eg nuclear pore forming structures, mitochondrial protein import structures). These membrane polypeptides are typically referred to as membrane proteins.

Since membrane proteins have the intrinsic ability to assemble at interfaces in combination with other amphiphiles, they are suited to the construction of biomimetic surfaces for use in biocompatible devices and biosensors. Biosensors incorporating membrane polypeptides have many potential applications including, by example and not by way of limitation, ligand based biosensors for clinical diagnostics; the detection of contaminants in water and environment; memory devices; screening devices for pharmaceutical applications; the provision of biologically functionalised surfaces; binding sites for, and this sensors for, small molecules such as drugs, pesticides, molecules required to be analysed during process control (i.e. food stuffs, fermenter products, chemicals); larger molecules such as proteins for research screening (eg array technology) or diagnostics (cancer markers, infectious disease markers, hormones); nucleic acids; carbohydrate polymers; cells such as pathogenic bacteria; eukaryotic cells such as cancer cells and small single or multicellular organisms especially parasites. Moreover, a biosensor may contain membrane polypeptides combined with other components independently attached to the surface of the biosensor which themselves act as specific binding sites and for which the membrane polypeptide provides a stable non-denaturing surface and/or a ion-channel dependent sensor function. Biosensors can be employed in high throughput screening for pharmaceutical applications using ion channel modulation or the other methods describe above.

Biosensors can provide an inert, stable, biologically compatible assembly of biologically functionalised surfaces including peptides, nucleic acids; proteins and other large molecules. These structures can be used in screening and biosensor systems. They may also be used to create surfaces compatible with cell culture or implantation in living tissue.

Additionally, enzymes may be engineered into the membrane polypeptides or co-assembled with the membrane polypeptides such that they can be functionally and precisely assembled at surfaces. This could have applications in bioreactor systems where catalytic surfaces are required or sensor systems where the enzymatic product is more easily detected than the substrate. The enzyme plus membrane polypeptide could be specifically printed or applied such that 1, 2 or even 3 dimensional spatial arrangements can be defined. If combined with flow systems this may allow for sequential enzymatic synthesis/degradation along a small scale bioreactor.

It will be apparent to the skilled artisan that this technology also has broad applicability to the provision of surfaces which allow the linking of membrane polypeptides to a substrate in a particular orientation and density which allow these surfaces to function as binding surfaces for a range of molecules the interaction of which can be monitored by established methods. For example, optical methods such as surface plasmon resonance; fluorescence; ellipsometry; or electrical methods such as spectroscopy impedance, cyclic voltametry, conductance measurement. Membrane polypeptides could be used in biosensors in devices to sense physical signals such as voltage, pressure or temperature.

The modifiable permeability of the biosensor could be used to allow the controlled release of molecules across the surface from a reservoir below the layer. A layer composed of thiolipids and membrane polypeptides could also be used to trap molecules such as drugs in a reservoir. A biological signal such as pH, protease activity or ligand binding could trigger the release of the drag. One example could be microbeads targeted to specific tissues which release drugs through the membrane polypeptide channel when they bind to or enter the target cell. The membrane polypeptide could also be engineered to carry peptide sequences which by binding to specific cellular receptors would target the microbead to specific tissues. This could be in addition to or separate from the drug release function.

Ionophores are polypeptides or protein structures with a tertiary and in many cases quaternary structure forming pores embedded in cell membranes. Ionophores function to control the flow of ionic currents in response to either electrical excitation (referred to as voltage gating) or the presence of stimulatory ligands, for example neurotransmitters (referred to as ligand gating).

An example of a group of functionally related membrane proteins is the porins which is a sub-group of the ionophores. Other groups include GPCRs, pentameric ligand gated channels, ABC transporters etc.

The signal transducing properties of ion-channels, combined with their high sensitivity and their minimal size, has led to the development of biosensors based on synthetic membrane structures incorporating ion-channel proteins. Although there is no difficulty in manufacturing these membranes incorporating ion-channels they are often expensive to obtain or are fragile and unstable.

Prior art biosensors (see U.S. Pat. No. 5,234,566; U.S. Pat. No. 5,736,342; U.S. Pat. No. 5,516,890; WO9725616) are based on the tethering of a biolayer to the surface of a substrate in such a way that a layer is left attached to the substrate (eg by the use of thio-lipids). These biolayers serve as a substrate into which ion-channel forming polypeptides can be inserted during or after formation to provide a functional biological transducer. A problem associated with the synthetic membranes of this type is that when used with large integral membrane proteins of biological origin they lack durability, are expensive to manufacture and protein density and orientation is poorly controlled. In a particular case the device of Cornell (Cornell et al., 1997) uses a fluid lipid bilayer composed of half membrane spanning lipids and membrane spanning lipids which is tethered to the surface of thiolipids. The membrane allows for ease of diffusion in the plane of the bilayer and this is exploited by the use of gramicidin peptides. These synthetic half membrane spanning ionophore peptides only allow ion flow when a dimer is formed spanning the whole membrane. Generally one monomer is tethered to the substrate and the upper monomer is connected to a receptor molecule. Binding to the receptor alters the amount of conducting dimers present and results in a conductance change. This allows for biosensors of high sensitivity to be manufactured.

BRIEF DISCLOSURE OF THE INVENTION

The present invention directly immobilises membrane-spanning proteins, for example, ion-channel forming membrane proteins, at the surface of a substrate to form a high density layer of coupled proteins to which is added a lipid layer to form a membrane structure. The combination of chemisorbed protein and amphiphile lipid layer provides a stable layer in which the normal protein structure and function are conserved. This is contrary to the teaching in the art, which taught that the direct tethering of membrane proteins to a substrate will result in the denaturation of the polypeptide thereby providing a non-functional membrane protein.

Biosensors constructed according to the invention have ease of manufacture and are more robust and are more widely applicable than prior art sensors since in addition to membrane based biosensor applications the method allows for the controlled assembly of dense, mimics of native protein layers with controlled orientation on solid substrates. The proteins can be engineered to incorporate specific functions in their exposed surfaces.

For example, according to the invention, we have engineered an ion-channel forming protein such that it can be directly coupled to a metal surface, in this example gold, to which is added thio-lipids which complete the membrane structure and provide a functional biosensor. One example uses the bacterial OmpF polypeptide which is modified to incorporate a cysteine amino acid which facilitates the linkage of the polypeptide to a treated substrate. It will be apparent that this technology can be applied to other ion-channel forming polypeptides and other membrane polypeptides using thiol containing amino acids. In particular any protein which presents a flat surface close to the membrane interface (such as the outer membrane proteins of bacteria or bacteriorhodopsin) may be considered suitable for this method. The polypeptides may naturally include a thiol containing amino acid or be genetically engineered to include a thiol containing amino acid. The amino acids may be naturally occurring or modified amino acids.

In comparison to the prior art of Cornell, the present invention relies upon large integral membrane proteins directly fixed to the substrate surface and lateral diffusion in the bilayer does not occur. Hence the role of the bilayer is to stabilise the assembled protein layer, reduce non-specific binding to the substrate surface and provide electrical insulation. Since the bilayer need not be fluid, the tethered lipids may comprise 100% of the lipids in the half bilayer next to the surface. The upper half bilayer is then completed with membrane phospholipids such as diphytanoyl-phosphatidylcholine. However, as the proteins employed all span the complete lipid bilayer, rather than being half-membrane spanning peptides (as in the prior art of Cornell), the option is available to form the entire membrane from tethered lipids capable of spanning the entire thickness of the membrane. The conductance changes observed by impedance spectroscopy when using porins as the membrane-spanning proteins in the present invention are due to changes in the pore of each protein and rely upon the intrinsic gating of individual channels rather than the formation and disruption of dimers. Furthermore since purified recombinant membrane proteins can be employed, the method offers a broad technique to create immobilised engineered protein surfaces that are not achievable with synthetic peptides of Cornell. The β-barrel membrane protein family are good targets for protein engineering and thus a wide variety of protein interfaces may be constructed in this manner.

In the context of the present invention the polypeptides which are directly coupled to the substrate are referred to as "membrane-spanning proteins". The implication of this is that the polypeptides are generally not simple linear short synthetic amino acid sequences with little or no secondary/tertiary structure (eg protein folding). The implication is also that the protein is of a size and shape which means that it would reside in a membrane and would extend at least mostly across the width of the membrane bilayer. It is generally expected that polypeptides which reside essentially only at or in one or other periphery of a membrane bilayer will not be advantageously useful in this invention. Similarly, very large/complex proteins which mainly reside outside a membrane bilayer but which may extend partly into the bilayer are unlikely to be advantageously useful in this invention. Those skilled in the art will appreciate that the term "membrane-spanning" should not be interpreted strictly so as to exclude from this invention proteins extending partially beyond the membrane boundaries or extending only across the majority of the region between the membrane boundaries.

STATEMENTS OF INVENTION

According to a first aspect of the invention there is provided a product comprising: a membrane-spanning protein; a lipid membrane formed from amphiphilic molecules and membrane-spanning protein molecules; and a substrate: characterised in that the membrane protein is directly coupled to the substrate.

In a preferred embodiment of the invention the product is a biosensor or protein array.

In a further preferred embodiment of the invention the membrane-spanning protein comprises an α-helix structure or a β-barrel structure.

Porins are outer membrane proteins which, in monomeric, dimeric or trimeric form, constitute a water-filled transmembrane channel ("pore"). This pore allows the passage of ions and numerous other, non-specific, molecules through a membrane. Porins are found in the outer membrane of mitochondria and in many Gram-negative bacteria. Porins include the OmpA family of polypeptides having an eight stranded β-barrel, and OmpF which is a homotrimer of 16 stranded β-barrels.

TonB dependent and related outer membrane transporters are also included in the scope of this invention. These proteins are usually monomeric polypeptides, are not channel forming and are highly specific for particular nutrients.

Membrane-spanning proteins can be modified to facilitate the coupling of the polypeptide to the substrate.

We have genetically engineered OmpF by the mutation glutamate 183 to cysteine (E183C). The insertion of a cysteine, or other thiol containing amino acid, into any of the periplasmic turns of the OmpF polypeptide will give similar results to those disclosed. More than one cysteine residue could be added to each protein to increase the interaction with the surface, hence this could be tailored to individual requirements. Insertion of cysteine into the extremities of the extracellular loops will also work but will result in a protein layer of the opposite orientation.

Synonyms of OmpF are: Porin ompF
Outer membrane protein 1A
Outer membrane protein 1A
Outer membrane protein B
Gene names are: OMPF or TOLF or CMLB or COA or CRY or B0929

We have also genetically engineered OmpA to insert a Lys residue.

In an embodiment of the invention the membrane-spanning protein may be alpha helix rich and has no large extra membrane projections on at least one of the two membrane surfaces. Examples whose high resolution structures are known include bacteriorhodpsin and the bacterial potassium channel KcsA. Many members of the GPCR family may be applicable to this form of immobilisation.

The membrane-spanning protein may be selected from those presented in Table 1 or Table 2.

The linking of a membrane-spanning protein directly to a substrate may be achieved by the reaction of a sulphur atom (found, for example, in cysteine) with a substrate, for example gold, by a direct sulphur-gold linkage. This results in a protein retaining functional activity. The substrate can be rendered hydrophobic by preincubation with a small hydrophilic thiol, for example β-mercaptoethanol or thio glycerol.

The porins are stable proteins and can be added to the surface in detergent solutions (such as SDS or Dodecyl-glucoside) which do not denature the protein but ensure that non specific hydrophobic interactions with the surface are reduced or do not occur.

The cooperative nature of the cysteine reaction means that the OmpF protein readily reacts with the pre-treated surface and is not inhibited by the presence of thiols. The cooperativity may arise from having three cysteines per trimer, or more than one cysteine per monomer. In general the self assembly properties of the proteins in creating a monolayer of protein with non-polar contacts between neighbouring proteins is likely to be important. This may explain the high density achievable. Additionally, the contact of the hydrophilic protein loops with the hydrophilic surface is non-denaturing and separates the core of the protein from the surface.

The protein layer is then further stabilised by adding amphiphiles to the surface, preferably thio-lipids, which will bond via a gold sulphur bond and fill the gaps between the proteins. This provides a membrane-like environment which satisfies the polypeptide's needs for hydrophilic and hydrophobic surfaces and thus ensures the stability of the protein.

In a further embodiment of the invention the lipid is a thiolipid.

The thiolipids are a very variable group. For example, ZD16, is based on dipalmitoylphosphatidic acid, which is extended at the lipid phosphate by a hydrophilic spacer chain of ethoxy groups of variable length, with a terminal disulfide group at the end of hydrophilic spacer. These anchor-bearing "thiolipids" can attach to substrates by forming stable substrate-sulfur bond. In this way we can couple lipid bilayers to substrates with the possibility of preserving a water layer between the substrate and the first monolayer.

Thiolipids without spacers such as 1,2-dipalmitoyl-sn-glycero-3-phosphothioethanol also have utility with respect to the biosensor of the invention. The lipid portion may be any fatty acid including branched chain (e.g. phytanoyl groups) or unsaturated (e.g. oleoyl) or a sterol such as cholesterol or the lipid may be based on a ceramide. The lipid portion may also consist of lipids such as those from archaea in which the membrane contains lipids which span its entire width from one aqueous phase to another.

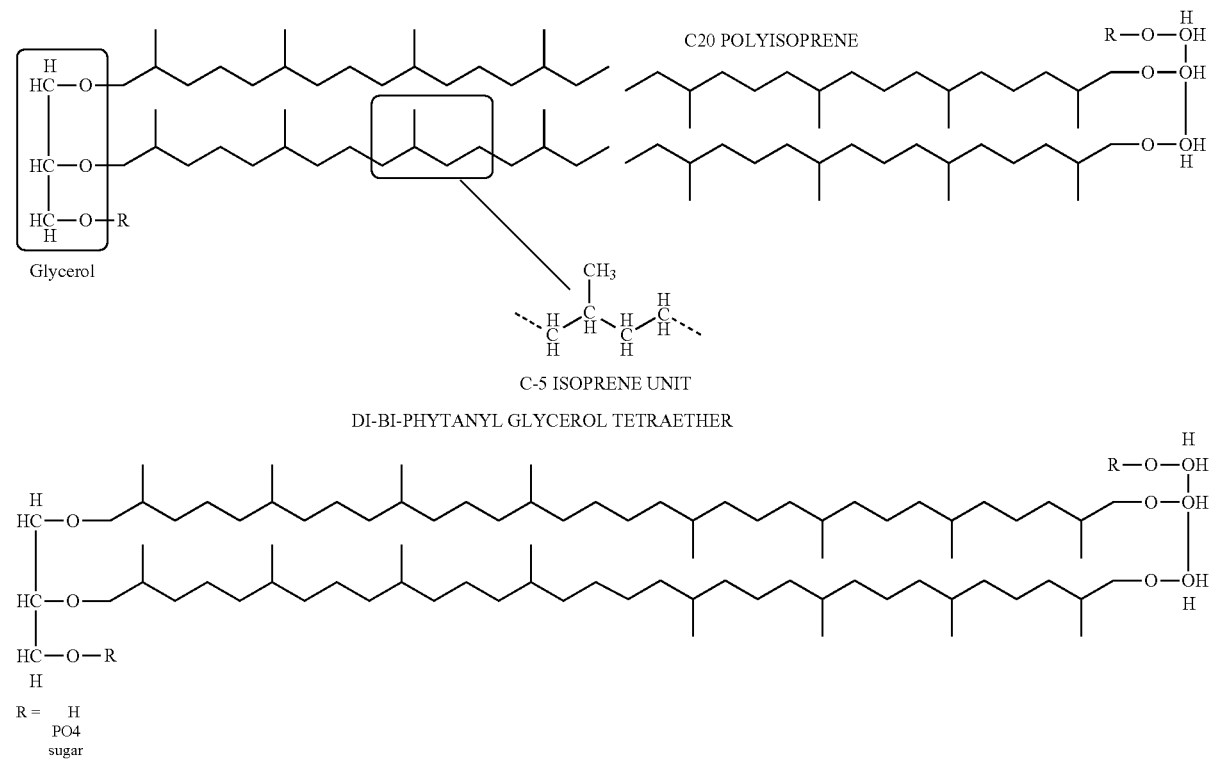

Thiolipids based upon this design will covalently link the entire membrane to the surface. Examples of this design are the Di-Bi-Phytanyl glycerol tetraethers which are found in species such as *Methanobacterium, Methanobrevibacter, Sulfolobus, Thermoplasma, Thermoproteus*. The hydrophilic groups may be any kind of chemical unit which links the thiol group to the hydrophobic groups. Preferably the carbon backbone is hydrophilic to stabilise the hydrophilic protein loops adjacent to it.

Preferably the thiolipid is selected from: 1,2-dipalmitoyl-sn-glycero-3-phosphothioethanol; 1,2-dioleoyl-sn-glycero-3-phosphoethanolamine-N-[3-(2-pyridyldithio)propionate]; 1,2-Dipalmitoyl-sn-Glycero-3-Phosphoethanolamine-N-[3-(2-pyridyldithio)propionate]; N-(14'-mercapto-1',11'-dioxo-3',6',9'-trioxa-12'-azatetradecyl)-2-oleoyl-1-palmitoyl-sn-glycero-3-phosphatidylethanolamine; (8'-mercapto-3',6'-dioxa-octyl)-1,2-dipalmitoyl-sn-glycero-3-phosphatidic acid.

The invention also includes the use of amphiphilic molecules other than lipids. Amphiphilic molecules have one or two hydrophilic head portions and at least one hydrophobic region and are typically referred to as surfactants. Examples are cationic surfactants (eg quaternary ammonium salts); anionic surfactants (eg organosulphate salts) and zwitterionic surfactants (eg phosphatidyl cholines). Other amphiphilic molecules include detergents, fatty acids. Less water soluble molecules such as alkane thiols may be suitable. These may terminate with a thiol at one end and a water soluble group such as a hydroxyl group or a sugar at the other. These may, for example, have carbon chain lengths between 10 and 18.

In a further embodiment of the invention the substrate is a metal. The metal may be selected from: gold; chromium; platinum; silver.

In a further embodiment of the invention the substrate is selected from: glass, silicon, hydrogen terminated silicon or plastic polymers.

It will be apparent to one skilled in the art that methods to generate mutations which delete or change codon usage are available. Modification of a membrane-spanning protein (such as an ion-channel forming polypeptide) means deletion, addition or substitution of at least one amino acid residue wherein the modification provides a protein capable of binding directly to a substrate to provide a product according to the invention.

In one embodiment of the invention OmpF is modified at position 183 of the amino acid sequence by mutation of glutamate to cysteine. This corresponds to position 205 of the unprocessed OmpF polypeptide and position 183 of the mature polypeptide.

There is provided a method for the production of the modified protein used in the invention, comprising:
i) providing a cell transformed/transfected with a nucleic acid molecule which is part of a vector adapted to facilitate recombinant expression of the protein;
ii) growing said cell in conditions conducive to the expression of said protein; and
iii) purifying said protein from said cell, or its growth environment.

The vector may encode, and thus said modified recombinant protein is provided with, a secretion signal to facilitate purification of the protein.

According to a further aspect of the invention there is provided a product comprising a biosensor.

The product may be a single element biosensor using electrochemical or optical methods to detect the specific interaction of a defined analyte, protein, nucleic acid, sugar, steroid etc with the engineered protein layer. It might consist of a protein/lipid layer on a gold surface combined with electronic circuitry or as part of a surface plasmon resonance device. The protein layer would, for example, contain binding sites for a specific antibody which is diagnostic of an infection. A sample of blood or other biological fluid could be applied to the surface via a wick which will filter out large particles, cells etc. On reaching the protein layer the binding would cause a change in the electrical or optical properties which could be read via an electronic output.

Another related product might be a sensor implanted in the body to monitor in real time the levels of specific biomolecules in blood or tissue. The device might consist of an electrical component containing a small (eg. <<1 mm diameter) gold electrode covered with the membrane protein layer. Binding of specific molecules would be read off as a change in the impedance properties.

The product may also be a device for making and analysing two dimensional arrays of proteins for analytical screening purposes. The device would include apparatus for the printing of modified proteins onto surfaces for the creation of the arrays. The arrays would then be used to screen samples containing proteins, small molecules, cells, enzyme inhibitors, nucleic acids which will bind specific sites on the array. The sites where protein has bound would be detected by surface plasmon resonance, fluorescence, mass spectrometry, electrochemical methods etc.

The product would allow for rapid screening of samples for a range of proteins and thus increase productivity in clinical or research labs.

Another product would be a bioreactor which used catalytic surfaces created by inserting catalytic domains into the membrane protein. Samples would be pumped by microfluidics along channels lined by immobilised catalytic proteins. In this way sequential modification of samples could be achieved and precise synthesis or modification of biological molecules achieve. Such a bioreactor could be formed on a micromachined silicon structure to modify small amounts of sample which would then be used for subsequent analysis. Fusions of enzymes and the membrane protein will also allow arrays of bioreactor spots to be used in high throughput screening.

A further product could be the creation of biocompatible surfaces for in vitro implantation or cell culture technology. For example, a coronary stent could have improved biocompatibility by being coated in a monolayer of engineered proteins which improve the interaction with epithelial cells. Other examples are artificial joints or continuous in vivo monitoring devices for controlled drag delivery A further example would be cell culture plates which are modified with a protein monolayer to encourage defined patterns of cellular growth. These may be from Petri dish size down to micro machined silicon devices. Applications of the product may involve the inducement of morphological changes in cells especially nerve cells or the patterned growth of different cells lines adjacent to one another to study and exploit cell-cell communication in research and analysis. The product would consist of patterned monolayers of engineered proteins which present surfaces recognised by each cell type. The patterned monolayers could be incorporated into a range of sizes of cell culture vessels.

The product of the invention could be produced from a ready made solution (not necessarily aqueous) of membrane proteins, also optionally with an amphiphile (detergent/lipid), which can be used to create controlled mono-molecular protein surfaces. The solution could consist of a defined mixture of proteins which would provide a similarly defined mixture of modified proteins on the surface. This would enable the manufacture of substrates with a controlled density of binding sites to be applied by self assembly with non-binding proteins acting as spacers.

A product according to the invention would be ready made gold surfaces bearing defined protein/lipid layers which could be utilised in a surface plasmon resonance biosensor.

According to a yet further aspect of the invention there is provided a method for the preparation of a product comprising:

i) treating a substrate with a hydrophilic coating agent;
ii) providing at least one membrane-spanning protein;
iii) bringing the protein into contact with the treated substrate under conditions for the coupling of the protein directly to the treated substrate;
iv) adding amphiphilic molecules to the protein-coupled substrate to form a lipid membrane.

In one method of the invention the product is a biosensor. In a further method of the invention the membrane protein is an outer membrane protein, such as a porin.

In the method of the invention the hydrophilic coating agent may be selected from: 2-mercaptoethanol; mercaptopropionic acid; 1-mercapto-2-propanol; 2,3 dimercapto-1-propanol; 2-mercapto-3-butanol; dithioerythritol(erythro-1,4-dimercapto-2,3-butanediol, DTE); Dithiothreitol (Cleland's Reagent, threo-1,4-dimercapto-2,3-butanediol, DTT); mixtures of DTE and DTT; thiol glycerol.

Preferably the coating agent is 2-mercaptoethanol.

Conditions for coating substrates may be varied. For example, the concentration of hydrophilic coating agent is between about 1 mM and 1M, preferably between about 50 mM and 500 mM, more preferably between about 100 mM and 200 mM. Incubation time may also vary from hours to many days without detrimental effects to the prepared surface.

Preferably the substrate is gold and the outer membrane polypeptide is a porin. More preferably still the porin is OmpF or modified OmpF. Preferably the amphiphilic molecule is a lipid, ideally thio-lipid.

According to an aspect of the invention there is provided a biosensor obtainable by the method according to the invention.

According to a further aspect of the invention there is provided the use of the biosensor according to the invention to detect at least one of following molecules: colicin N R-domain; polypeptides; antigenic polypeptides; antibodies or fragments of antibodies; receptors; ligands; antibiotics; drugs; pesticides; sugars; amino acids; fatty acids; peptides; hormones; steroids; nucleic acids (DNA, RNA, cDNA); peptide nucleic acids; metals; inorganic ions.

An embodiment of the invention will now be provided by way of example only and with reference to the following Figures and Tables wherein:

Table 1 represents porin genes of Gram-ve bacteria;
Table 2 represents Ton B dependent receptors from various bacterial species;
FIG. 1 is the nucleic acid sequence encoding OmpF (wild type) and the encoded protein sequence of OmpF; [SEQ ID No. 1] and [SEQ ID No. 2];

FIG. 2 represents binding of anti OmpF polyclonal antibodies to tethered OmpF-Cys;

MATERIALS AND METHODS

Protein Purification

Wild type OmpF (OmpF-WT) from *E coli* BE3000 was produced as previously described using the plasmid pGBF96 (Bainbridge, G., Mobasheri, H., Armstrong, G. A., Lea, E. J. A. and Lakey, J. H. (1998)) and purified in SDS detergent or subsequently resuspended in Octyl-POE. The mutant of OmpF with a single cysteine in turn 1 (OmpF-CYS) was created using the QuikChange™ method (Stratagene).

Mutagenesis of OmpF

The mutagenesis used two complementary 37 mer oligonucleotides which coded for a TGT cysteine codon instead of a GAA glutamate codon.

```
Forward
                                         [SEQ ID No. 3]
5'-GGTTCTATCAGCTAC TGTTACGAAGGCTTTGGTATCG-3'

Reverse
                                         [SEQ ID No. 4]
3'-CCAAGATAGTAGATG ACAATGCTTCCGAAACCATAGC-5'
```

These mutagenic primers were used with the plasmid pGBF96 in the QuikChange protocol described in the QuikChange kit supplied by Stratagene. The transformants in XL1-blue *E coli* cells were used to produce pure plasmid DNA by use of Promega Wizard SV miniprep kits. The OmpF gene was sequenced by an ABI-Prism 377 device in the University of Newcastle Facility for Molecular Biology.

The mutation in the OmpF BE3000 gene caused by our introduction of an XbaI restriction site is Lysine279 to Arginine (K279R). Thus although the DNA sequence is different at "wobble" positions from the database *E. Coli*

OmpF DNA sequence, the protein used in the example differs from this database example only by the mutations E183C and K279R.

Amphiphilic Agents

The phospholipids used were di-oleoyl phosphatidyl choline (from the Sigma Chemical Company, Fancy Road Poole Dorset UK) or Di-phytanoyl phosphatidyl choline (from Avanti Polar Lipids Birmingham Ala. USA). The thiolipid (laboratory designation ZD16) was of the formula below and synthesised using the methods previously described in Lang (1994).

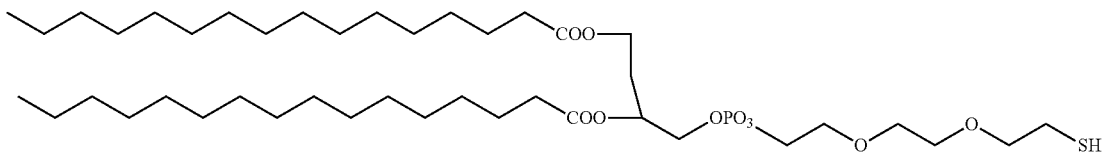

Surface Plasmon Resonance. (SPR)

Gold chips for the Biacore were either plain gold Biacore J1 type (Biacore AB, St Albans UK) or recycled Biacore chips cleaned with piranha solution. Glass slides of refractive index 1.7 were cleaned by sonication in a water bath sonicator in 2% Helmanex cleaning solution (Helma GmbH Germany) followed by extensive rinsing in Nanopure water and stored in ethanol with or without 2-mercaptoethanol until required. Residual ethanol was evaporated under nitrogen and the slide was placed in an Edwards High Vacuum Evaporator. When the vacuum reached $5 \times 10^{-6}$ millibar the slide was coated on one side by a 3 nm chromium layer by evaporation of chromium. The system was allowed to cool for 15 minutes before a 100 nm layer of gold was evaporated on top of the chromium substrate. Following a further 15 minutes cooling the vacuum was relieved by argon and the slide was assembled into the SPR device. This consisted of placing the slide with the gold face forming the remaining side of a Teflon cuvette which was open towards the top for exchange of fluids. A Leica 60° prism was placed on the opposite side of the slide with the junction completed by refractive index matching fluid. The assembly was clamped together and placed in the SPR device. Solutions were added and removed from the cuvette by Pasteur pipette or graduated syringe. The minimum of reflected laser light was detected by scanning the reflected signal with a photodiode connected to a personal computer. The exact minimum was calculated using curve fitting. To follow time dependent changes in SPR signal the diode angle was set to a value approximately 2 degrees below the initial minimum where the intensity change per unit angle is large. Increases in the angle of the minimum were thus represented as increases in signal strength.

The Biacore experiments were carried out with the machine in the standard format. The mercaptoethanol treated chips were placed in the machine and the required solutions pumped over the chip at a defined flow rate The flow rates are 1 μl per minute for the protein/thiolipid assembly steps and 30 μl per minute for the binding assays with colicin N R-domain. Two lanes in series were used. Time dependent changes in SPR signal were measured as changes in resonance units as defined in the Biacore Users Manual.

Impedance Spectroscopy (I.S.)

Impedance spectroscopy was carried out in an electrochemical cell comprising a membrane covered gold electrode and a reference Ag/AgCl electrode in 0.1M KCl, 5 mM sodium phosphate buffer pH 7.4 The surface area of the gold disk electrode was $3.34 \times 10^{-2}$ cm$^2$. No DC voltage was applied. A sinusoidal voltage of 10 mV (RMS) was applied to the cell at 199 successive frequencies equally spaced on a logarithmic scale from 1 Hz to 20 kHz. The resulting current was recorded via a phase sensitive lock-in amplifier to calculate the complex impedance and admittance.

Fourier Transform Infra-Red Spectroscopy (FTIR).

Samples for FTIR analysis were assembled on Helmanex cleaned glass microscope slides onto which was evaporated 3 nm of chromium followed by 100 nm of gold as for the SPR experiment apart from the gold thickness. Pretreatment with mercaptoethanol was as for the SPR glass slides. Assembly of protein, thiolipid or phospholipid was performed by laying the solution onto the slide which was placed in a plastic Petri dish and covered to prevent evaporation. Successive layers were assembled by replacement of the initial solution by the subsequent solution without drying or rinsing. Before spectra were collected the slides were washed under running Nanopure water, dried under argon and immediately placed in the spectrometer. Infra red spectra were recorded using a Broker IFS 28 spectrometer equipped with an HgCdTe detector. One thousand scans were recorded at 1 cm$^{-1}$ resolution and apodised with a boxcar function. Background spectra were recorded from the respective bare supports. The corrected spectra were Fourier smoothed to 1 cm$^{-1}$ resolution with triangular apodisation. The reflectance absorbance spectra a molecular layers on gold was recorded at an angle of incidence of 85° using only parallel-polarised light. All peak positions were derived from second derivative spectra. For further details of the technique, see Boucheva (1997).

Binding of Anti-OmpF Polyclonal Antibodies to OmpF-Cys

FIG. 2 shows the binding of anti-OmpF loop 6 rabbit polyclonal antibody (at two concentrations) to OmpF-Cys tethered to gold and embedded in the fluid hybrid bilayer of DOPC (top layer, towards the solution) and thiolipids (bottom layer, tethered to gold). Sensorgrams were recorded in PBS running buffer at flow rate of 30 μl/min on a Biacore X (Biacore AB, Uppsala, Sweden). Fitted black curves for a Langmuir 1:1 binding model are superimposed. The association rate constant $K_a$ was evaluated at $4.4 \times 10^4 M^{-1} s^{-1}$, and the dissociation rate constant $K_d$ was $6.0 \times 10^{-5} s^{-1}$ for a calculated affinity constant $K_D$ of 1.4 nM. The binding interaction indicates that the protein is immobilized with its extracellular loops exposed.

Example 1

Immobilisation Experiment using OmpF-Cys.

A plain gold surface is first treated with β-mercaptoethanol (1 mM in buffer A (100 mM NaCl, 100 mM Na phosphate pH 7.0.)), followed by a wash with buffer A. OmpF-Cys in Octyl-POE (0.3 mg/ml) was then applied to the surface and rapidly bound to the surface achieving an equilibrium. Washing with Buffer A removes the previous buffer effect and leaves an increased signal of 1000 resonance units (this can be increased with longer incubation). Next the surface is washed with 0.05% SDS until no more protein is removed. OmpF is stable in SDS and this treatment removes non-specifically bound OmpF and leaves covalently bound trimers of OmpF on the gold surface. Any wild type protein which binds non-specifically to gold surfaces is washed off by this treatment. Thiolipid (ZD16) added from 1% Octyl-glucoside solution binds via its thiol group to the remaining gold surface and completes a monolayer of covalently bound lipid and protein. Addition of thiolipid to a control gold layer shows a much higher level of lipid binding confirming that OmpF-Cys and ZD16 compete for the surface layer. Addition of phosphatidylcholine vesicles completes the bilayer since they attach and become disrupted on the exposed hydrophobic surface. We have since found that incubation ex situ overnight followed by washing in the Biacore device provides the most complete layer. Further treatment with β-mercaptoethanol does not dislodge the layers showing that the self assembled proteins and lipids are effectively irreversibly bound to the surface.

Example 2

Data from the SPR device is provided directly in angle shifts of the SPR signal on a time axis. This showed similar results to the Biacore data but can be related directly to surface densities which can then be used to calculate the mean thickness of the layer.

The protein immobilisation gave an angle shift of 0.31°+/− 0.17 whether the protein was dissolved in SDS or Octyl-POE (0.3 mg/ml). This was a very reproducible result which confirms the efficiency of the self-assembly process. The angle shift expected from a two-dimensional crystal of OmpF is 0.75° and thus the protein is immobilised at 40% of the maximum coverage. This is a very high level considering that no special precautions are taken to maximise self assembly, such as preformation of 2D crystals.

Thiolipid self assembly results in another 0.42°+/−0.06 increase and PC addition is about 0.30°+/−0.17.

The values are very constant and show that a very reproducible system of self assembly has been created.

Example 3

FTIR spectra was collected of porin timers directly self assembled (1% Octyle-POE 0.3 mg/ml OmpF-Cys) for one hour at room temperature and after a second stage of self-assembly using 1 mg/ml ZD-16 thiolipid in 9 omM Octyl-glucoside. Neither sample showed spectra with beta structure remaining.

Pre-treating the gold with β-mercaptoethanol (10 mM in ethanol) (at least 1 hour but now these surfaces are stored in 10 mM β-mercaptoethanol until use) causes an improvement in the retention of OMPF secondary structure. This was followed by OmpF-Cys self assembly as above followed by rapid replacement of this solution by the ZD16 solution. This self assembles the thiolipid layer without a drying step and also solubilises and removes non-specifically bound protein. The result of this is a spectrum which closely resembles the published spectrum (Nabedryk et al., 1988) and confirms that the secondary structure of OmpF is retained by this process. Incubation with 1 mg/ml phosphatidylcholine vesicles in buffer A for 1 hour generates an extra intensity in the peak at a wavenumber of 1740 cm-1. This is from the lipid and exactly doubles the existing thiolipid peak showing that the surface layer of the bilayer has been completed by this process. The protein spectrum showed a slight increase in beta secondary structure.

Even without subsequent thiolipid assembly the pre treatment with β-mercaptoethanol causes a significant improvement in retention of secondary structure. A similar benefit could be achieved by using another small hydrophilic Thiol molecule.

Example 4

The maximum density of self assembled OmpF-Cys followed by thiolipid provides a layer which is very conducting and this cannot be analysed by IS. The impedance spectroscopy can be measured at lower protein densities and clear results were obtained using a layer made using a 1 hour incubation with a 0.003 mg/ml OmpF-Cys solution, this is 100 fold less than the concentration used above. At 100 Hz the resistance of the surface layer dominates the real part of the signal. Addition of $10^{-6}$ M colicin R domain caused the resistance to increase showing that the layer is being blocked by the protein interaction. This effect is concentration dependent and resembles the measured affinity of the previous paper.

Binding of colicin N R domain is being studied by SPR in Newcastle and confirms the impedance data shown here.

Example 5

Self-Assembly of Refolded OmpA Monomeric Porin Transmembrane-Domain Layers on Gold.

In order to use outer membrane receptor proteins in the development of membrane protein monolayers for bio-nanotechnology, we need to refold the proteins in vitro prior to assembling them on surfaces. Here we show that the outer membrane protein OmpA refolded by published methods can be assembled in the protein-thiolipid layers already demonstrated for OmpF. The result also shows that monomeric OMP's such as OmpA can be immobilised using the same methods as for trimeric porins.

Cloning

The coding sequence of mature OmpA (1-147) was amplified from *Escherichia coil* XL1-Blue (Stratagene) genomic DNA using colony PCR and the following primers Forward 5'-TTTTCTCGAGCTGTGCTCCGAAAGATAACACC-3' [SEQ ID No. 5] Reverse 5'-TTTTGCGCAAAGTGCCACGGCCTCGACCTCG-3' [SEQ ID No. 6] The primers include MluI and XhoI restriction sites respectively; which allowed cloning into the pET8c vector based upon the pET3c vector from Novagen. The expressed protein thus contains an N-terminal insertion of an MHHHHHHSS sequence [SEQ ID No. 7] coded by the plasmid and an additional Cys residue coded by the primer, and amino acids 1-147 of the mature OmpA protein. The plasmid was named pET8c-(CysOmpA1-147). The absence of the natural signal peptide means that the protein is expressed in the cytoplasm and forms inclusion bodies (Arora et al., 2001; Pautsch & Schulz, 2000).

The protein was expressed in BL21 DE3 pLysE (Novagen) using Luria broth and 100 μg/ml Ampicillin and 30 μg/ml Chloramphenicol. 6 litres of culture were incubated in Erlenmeyer flasks until the OD reached 0.6 when OmpA expression was induced by IPTG. After a further three hours growth the cells were harvested by centrifugation, broken by French Press and unbroken cells removed by a low speed centrifugation, (3000 rpm 10 mins). The supernatant was then centrifuged at 10,000 rpm in Beckman 55.2 rotor for 1 hour at 4° C. This crude inclusion body sample was washed three times by homogenising in 20 mM Tris pH 8.0 1% Triton X-100 and centrifuging at 8000 rpm for 1.5 hours (twice) and for 30 min (final) to yield a pure inclusion body preparation. This pellet was resuspended in 20 ml buffer (20 mM Tris pH 8.0, 8.0 M urea) and 20 ml isopropanol homogenised at 55° C. for 30 min. The homogenate was centrifuged at 38,000 rpm for 1.5 h at 4° C. The supernatant contained the solubilised His-Cys-OmpA1-147. The protein was further purified using Ni-agarose column and elution using imidazole. The protein was a single band on SDS-PAGE and its identity was confirmed by Western Blot using an anti-His tag antibody (SIGMA). Isopropanol was removed by dialysing the protein sample into a solution of 8M urea, 20 mM Tris, pH 8.0 and 1% v/v Genapol (Fluka) using Spectra-Por 6-8,000 MW dialysis tubing.

The protein concentration at this stage was 0.34 mM. The protein was refolded by dilution into an 200 fold molar excess of DG (n-docecyl-β-D-glycopyranoside, Calbiochem) at pH 8.1 following the procedures of Kleinschmidt et al., (1999). The refolded protein was then examined by circular dichroism spectroscopy which showed it to contain largely β-structure as expected from a fully refolded OmpA transmembrane domain. The protein was also resistant to proteolysis which is another property of a folded OmpA monomer.

Finally its was shown by SPR that the protein assembles on gold electrodes, and that thiolipids can be added to complete the monolayer as shown for OmpF layers. The results demonstrate that refolded monomeric porins such as OmpA can be used in the same manner as previously described for OmpF.

A gold J1 chip was cleaned with Piranha solution (9% v/v $H_2O_2$ and 70% conc $H_2SO_4$), rinsed with ethanol and water and dried with nitrogen. In the Biacore-X surface plasmon resonance spectrometer the chip was washed with 0.05% SDS solution, then 0.2% β-mercaptoethanol to provide the hydrophilic layer. After a second SDS wash the folded protein His-Cys-OmpA(1-147) at 0.2 mg/ml in n-docecyl-β-D-glucopyranoside showed strong binding to the surface. A subsequent SDS wash removed non-specifically bound protein and this was followed by a second assembly step of thio-lipid ZD-16 (0.5 mg/ml in 1% Octyl-polyoxyethylene 2.5 (Bachem)) to complete the protein-lipid layer.

REFERENCES

1. Stora, T., Lakey, J. H. and Vogel, H. (1999). Ion-Channel Gating in Transmembrane Receptor Proteins: Functional Activity in Tethered Lipid Membranes. *Angew. Chem. Int. Ed.* 38(3), 389-392.

2. Cornell, B. A., Braach-Maksvytis, V. L. B., King, L. G., Osman, P., Raguse, B., Wieczorek, L. and Pace, R. J. (1997). A biosensor that uses ion-channel switches. *Nature* 387(6633), 580-583.
3. Bainbridge, G., Mobasheri, H., Armstrong, G. A., Lea, E. J. A. and Lakey, J. H. (1998). Voltage gating of *Escherichia coli* porin; a cystine scanning mutagenesis study of loop 3. *Journal Of Molecular Biology* 275, 171-176.
4. Evans, L. J. A., Cooper, A. and Lakey, J. H. (1996). Direct measurement of the association of a protein with a family of membrane receptors. *Journal Of Molecular Biology* 255(4), 559-563.
5. Nabedryk, E., Garavito, R. M. and Breton, J. (1988). The orientation of beta-sheets in porin—a polarized fourier-transform infrared spectroscopic investigation. *Biophysical Journal* 53(5), 671-676.
6. Evans, L. J. A., Labeit, S., Cooper, A., Bond, L. H. and Lakey, J. H. (1996). The central domain of colicin N possesses the receptor recognition site but not the binding Affinity of the whole toxin. *Biochemistry* 35(48), 15143-15148. Stora, T., Lakey, J. H. and Vogel, H. (1999). Ion-Channel Gating in Transmembrane Receptor Proteins: Functional Activity in Tethered Lipid Membranes. *Angew. Chem. Int. Ed.* 38(3), 389-392.
7. Lang, H., Duschl, C., and Vogel, H. (1994). "A new class of thiolipids for the attachment of lipid bilayers on gold surfaces." *Langmuir*, 10(1), 197-210.
8. Boncheva, M., and Vogel, H. (1997). "Formation of stable polypeptide monolayers at interfaces: Controlling molecular conformation and orientation." *Biophysical Journal*, 73(2), 1056-1072.
9. Arora, A., Abildgaard, F., Bushweller, J. H. & Tamm, L. K. (2001). Structure of outer membrane protein A transmembrane domain by NMR spectroscopy. *Nature Structural Biology* 8(4), 334-338.
10. Kleinschmidt, J. H., Wiener, M. C. & Tamm, L. K. (1999). Outer membrane protein A of *E-coli* folds into detergent micelles, but not in the presence of monomeric detergent. *Protein Science* 8(10), 2065-2071.
11. Pautsch, A. & Schulz, G. E. (2000). High-resolution structure of the OmpA membrane domain. *Journal Of Molecular Biology* 298(2), 273-282.

TABLE 1

Examples of Porin proteins suitable for use in the invention
Species (total number of proteins of this class so far identified in this species)

siphoviridae pa (1)
lambda phage group p21 (1)
Ectothiorhodospira vacuolata (1)
Vibrio cholerae (1)
Photobacterium profundum (1)
Haemophilus influenzae (30)
Pasteurella multocida (7)
Rahnella aquatilis (2)
Salmonella typhimurium (4)
Enterobacter cloacae (1)
Salmonella typhi (5)
Citrobacter freundii (1)
Calymmatobacterium granulomatis (1)
Klebsiella pneumoniae (7)
Yersinia pestis (2)
Xenorhabdus nematophilus (1)
Klebsiella oxytoca (1)
Escherichia coli (9)
Serratia marcescens (2)
Burkholderia cepacia (1)
Eikenella corrodens (1)
Neisseria polysaccharea (1)

TABLE 1-continued

Examples of Porin proteins suitable for use in the invention
Species (total number of proteins of this class so far identified in this species)

Neisseria lactamica (2)
Neisseria gonorrhoeae (91)
Neisseria flavescens (2)
Neisseria sicca (2)
Neisseria meningitidis (160)
Bordetella pertussis (1)
Rhodobacter blastica (1)
Rhodobacter capsulatus
Brucella sp.;
Chlamydia sp
Shigella
Comamonas acidovorans
Aeromonas
Thermotoga maritima
OmpA 8 stranded beta barrel proteins and homologous membrane proteins Chlamydophila pneumoniae (1)
Chlamydia trachomatis (1)
Helicobacter pylori (5)
Haemophilus influenzae (4)
Haemophilus sp (1)
Pasteurella haemolytica (1)
Haemophilus parainfluenzae (1)
Pasteurella multocida (1)
Haemophilus somnus (1)
Haemophilus ducreyi (3)
Actinobacillus pleuropneumoniae (1)
Actinobacillus actinomycetemcomitans (1)
Vibrio alginolyticus (2)
Vibrio cholerae (1)
Vibrio parahaemolyticus (3)
Methylococcus capsulatus (1)
Aeromonas salmonicida (2)
Pseudomonas syringae (1)
Moraxella catarrhalis (1)
Pseudomonas aeruginosa (3)
Pseudomonas putida (2)
Pseudomonas fluorescens (7)
Escherichia vulneris (3)
Escherichia hermannii (1)
Escherichia fergusonii (1)
Escherichia blattae (1)
Salmonella typhimurium (2)
Shigella dysenteriae (1)
Serratia odorifera (1)
Enterobacter aerogenes (2)
Citrobacter freundii (1)
Klebsiella pneumoniae (1)
Serratia marcescens (1)
Escherichia coli (6)
Legionella pneumophila (1)
Neisseria gonorrhoeae (1)
Neisseria meningitidis (1)
Leptothrix discophora (1)
Bordetella avium (1)
Brucella abortus (1)
Bartonella bacilliformis (1)
Sinorhizobium meliloti (1)
Rickettsia prowazekii (1)
Aquifex aeolicus (3)
Treponema phagedenis (1)
Borrelia burgdorferi (2)
Treponema pallidum (3)
Sugar selective porins Vibrio parahaemolyticus (1)
Vibrio cholerae (1)
Aeromonas salmonicida (1)
Yersinia enterocolitica (1)
Klebsiella pneumoniae (2)
Salmonella typhimurium (2)
Escherichia coli (2)

TABLE 1-continued

Examples of Porin proteins suitable for use in the invention
Species (total number of proteins of this
class so far identified in this species)

Nucleoside specific channel forming protein TSX

*KLEBSIELLA PNEUMONIA*
*ENTEROBACTER AEROGENENES*
*ESCHERICHIA COLI*
*SALMONELLA TYPHIMURIUM*

There are more than 340 identified genes which code for Gram-ve porins, of these many are variants of *Neisseria meningitidis* outer membrane porins which show great variability in their outer loops. The following list is by species Additional porins, which have little sequence homology, are found at the end of the list Figures in brackets are the total number of porin-like genes identified in that species. Some proteins may not be true porins.

TABLE 2

TonB dependent receptors which may be immobilised by the method
have been identified in the following species of bacteria
Species (total number of proteins of this
class so far identified in this species)

*Helicobacter pylori* (6)
*Campylobacter coli* (1)
*Haemophilus influenzae* (17)
*Pasteurella haemolytica* (1)
*Haemophilus ducreyi* (3)
*Actinobacillus pleuropneumoniae* (5)
*Vibrio vulnificus* (1)
*Vibrio anguillarum* (1)
*Vibrio orientalis* (1)
*Vibrio cholerae* (3)
*Aeromonas salmonicida* (1)

TABLE 2-continued

TonB dependent receptors which may be immobilised by the method
have been identified in the following species of bacteria
Species (total number of proteins of this
class so far identified in this species)

*Pseudomonas stutzeri* (1)
*Moraxella catarrhalis* (4)
*Acinetobacter* sp (1)
*Pseudomonas aeruginosa* (11)
*Pseudomonas putida* (2)
*Shewanella* sp (1)
*Stenotrophomonas maltophilia* (1)
*Salmonella typhimurium* (2)
*Shigella dysenteriae* (1)
*Pectobacterium chrysanthemi* (1)
*Yersinia pseudotuberculosis* (1)
*Citrobacter freundii* (1)
*Yersinia enterocolitica* (4)
*Erwinia amylovora* (1)
*Salmonella paratyphi* (1)
*Salmonella cholerae* (1)
*Yersinia pestis* (2)
*Serratia marcescens* (1)
*Escherichia coli* (17)
*Neisseria gonorrhoeae* (3)
*Neisseria meningitidis* (12)
*Bordetella pertussis* (1)
*Bordetella bronchiseptica* (3)
*Paracoccus denitrificans* (1)
*Sphingomonas aromaticivorans* (3)
*Bradyrhizobium japonicum* (1)
*Rhizobiaceae* sp (1)
*Synechocystis* sp (3)
*Proteobacteria* sp (1)

---

The invention claimed is:

1. A product comprising:
   a membrane-spanning protein;
   a lipid membrane formed from amphiphilic molecules and membrane-spanning protein molecules; and
   a solid substrate, wherein the membrane-spanning protein is coupled directly to the solid substrate by a covalent coupling.

2. The product according to claim 1 wherein at least some of the amphiphilic molecules are coupled directly to the solid substrate by a covalent coupling.

3. The product according to claim 1 wherein the protein is coupled to the solid substrate via at least one exposed cysteine residue located in the periplasmic side of the protein.

4. The product according to claim 1 wherein the product is a biosensor.

5. The product according to claim 1 wherein the product is a protein array.

6. The product according to claim 1 wherein the protein comprises a polypeptide of more than 20 L-amino acid residues purified from a cell extract.

7. The product according to claim 1 wherein the protein comprises a β-barrel structure.

8. The product according to claim 1 wherein the protein is an ion channel forming protein (ionophore).

9. The product according to claim 1 wherein the protein is an engineered (recombinant) protein into which has been introduced, by insertion or mutation, at least one exposed cysteine residue located in the periplasmic side of the protein.

10. The product according to claim 8 wherein the protein is a porin.

11. The product according to claim 1 wherein the amphiphilic molecules comprise or consist of thiolipid.

12. The product according to claim 11 wherein the thiolipid is selected from the group consisting of: 1,2-dipalmitoyl-sn-glycero-3-phosphothioethanol; 1,2-dioleoyl-sn-glycero-3-phosphoethanolamine-N-[3-(2-pyridyldithio)propionate]; 1,2-Dipalmitoyl-sn-Glycero-3-Phosphoethanolamine-N-[3-(2-pyridyldi-thio)propionate]; N-(14'-mercapto-1',11'-dioxo-3',6',9'-trioxa-12'-azatetradecyl)-2-oleoyl-1-palmitoyl-sn-glycero-3-phosphatidylethanolamine; (8'mercapto-3',6'-dioxa-octyl)-1,2-dipalmitoyl-sn-glycero-3-phosphatidic acid; and ZD16 having the formula:

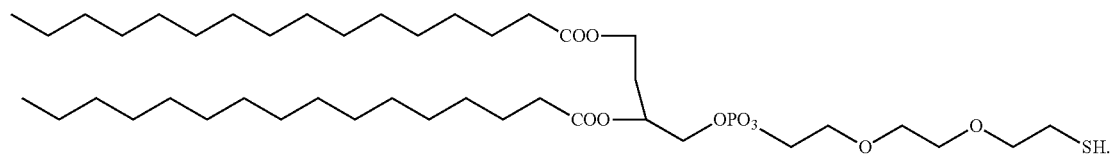

13. The product according to claim 1 wherein the solid substrate is a metal.

14. The product according to claim 13 wherein the metal is selected from: gold; chromium; platinum; silver.

15. A method for the preparation of a product according to claim 1 comprising:
  i. treating a solid substrate with a hydrophilic coating agent;
  ii. providing at least one membrane-spanning protein;
  iii. bringing the protein into contact with the treated solid substrate under conditions for the covalent coupling of the protein directly to the treated solid substrate;
  iv. adding amphiphilic molecules to the protein-coupled substrate to form a lipid membrane.

16. The method according to claim 15 wherein the hydrophilic agent is a thiol.

17. A product obtainable by a method comprising the steps of:
  i. treating a solid substrate with a hydrophilic coating agent;
  ii. providing at least one membrane-spanning protein;
  iii. bringing the protein into contact with the treated solid substrate under conditions for the covalent coupling of the protein directly to the treated solid substrate;
  iv. adding amphiphilic molecules to the protein-coupled substrate to form a lipid membrane.

18. The product of claim 1, wherein the protein is a modified OmpA from *E. coli*.

* * * * *